United States Patent [19]

Polaschegg

[11] Patent Number: 4,713,171
[45] Date of Patent: Dec. 15, 1987

[54] APPARATUS FOR REMOVING WATER FROM BLOOD

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 574,492

[22] Filed: Jan. 27, 1984

[30] Foreign Application Priority Data

Jan. 28, 1983 [DE] Fed. Rep. of Germany ....... 3302804

[51] Int. Cl.⁴ .................... A61M 1/14; A61M 1/34; B01D 13/00
[52] U.S. Cl. ................ 210/110; 210/321.3; 210/929; 422/44
[58] Field of Search .............. 210/40, 321.1–321.3, 210/929, 433.2, 109, 110, 257.2; 604/4, 5, 6, 27, 28, 29, 30, 31; 128/DIG. 3; 422/45, 48, 44

[56] References Cited

U.S. PATENT DOCUMENTS

| | | | |
|---|---|---|---|
| 3,007,416 | 11/1961 | Childs | 128/DIG. 3 |
| 3,218,979 | 11/1965 | Baldwin | 128/DIG. 3 |
| 3,459,176 | 8/1969 | Leonard | 128/2 |
| 3,727,612 | 4/1973 | Sayers et al. | 128/214 |
| 3,791,767 | 2/1974 | Shill | 417/389 |
| 3,811,800 | 5/1974 | Shill | 417/478 |
| 3,902,490 | 9/1975 | Jacobsen et al. | 210/929 |
| 4,062,360 | 12/1977 | Bentley | 128/DIG. 3 |
| 4,231,366 | 11/1980 | Schael | 604/4 |
| 4,231,871 | 11/1980 | Lipps et al. | 210/90 |
| 4,333,454 | 6/1982 | Hargest, III | 604/30 |
| 4,334,988 | 6/1982 | Milligan | 210/929 |
| 4,370,983 | 2/1983 | Lichenstein | 210/321.2 |
| 4,490,134 | 12/1984 | Troutner | 604/4 |

FOREIGN PATENT DOCUMENTS

2455971  8/1976  Fed. Rep. of Germany .
3115299  11/1982  Fed. Rep. of Germany .
3131075  2/1983  Fed. Rep. of Germany .
3205499  9/1983  Fed. Rep. of Germany .

OTHER PUBLICATIONS

Gloeckner, W. M.; "Kontinuierliche Haemofiltration. Eine Praxisbezogene Einfuehrung", *Wissenschaftliche Informationen, Fresenius, Anaesthesie*, vol. 15, pp. 216–224.

Hospal. Prospectus for Biospal SCU/CAVH Filter, Hospal Medical Corp., N.J.

Cavanaugh et al.; "Hemodialysis Blood Transport System"; IBM Technical Disclosure Bulletin, vol. 19, No. 3; 8/76.

*Primary Examiner*—Barry S. Richman
*Assistant Examiner*—C. M. Delahunty
*Attorney, Agent, or Firm*—Townsend and Townsend

[57] ABSTRACT

Apparatus for removing water from blood, advantageously by the single-needle method, in which by means of an air-operated bellows pump blood is sucked into an expandable pump chamber and thereafter water is forced into a hemofilter and collected in an ultrafiltrate measuring chamber to which a collecting bag is connected. The inlet and the outlet of the ultrafiltrate measuring chamber to which a collecting bag is connected. The inlet and the outlet of the ultrafiltrate measuring chamber can be opened and closed by clamps controlled in opposite phase and the amount of ultrafiltrate collected in the ultrafiltrate measuring chamber can be controlled and determined. The ultrafiltrate measuring chamber is divided by a hose-like wall into two chamber portions, one chamber portion receiving filtrate and the other chamber portion being adapted in a preferred embodiment to receive infusion solution. Thus, the infusion solution can be proportioned and supplied to the patient in volume equivalent manner.

22 Claims, 5 Drawing Figures

APPARATUS FOR REMOVING WATER FROM BLOOD

BACKGROUND OF THE INVENTION

The invention relates to an apparatus for removing water from blood in an extracorporeal circuit, comprising a filter which is connected on the blood inlet and outlet side via a supply line and an offtake line to at least one blood connection, the supply line having a blood pump and a clamp disposed upstream and downstream of the blood pump and the offtake line having a further clamp and a throttle means.

In the field of intensive medicine high-caloric nutrition frequently leads to hyperhydration of patients and thus to a drop in blood pressure which leads to failure in the filtration performance of the kidneys. To dehydrate the latter it is therefore possible to use the already known usual apparatuses such as hemofiltration machines or volume-controlled dialysis machines which generally are employed for pure dialysis in which apart from the withdrawal of water a cleaning of the blood from metabolism products takes place. Due to this specific use these known machines are tailored to this specific purpose and are made relatively complicated so that it is practically impossible for untrained personnel to Examples of such aforementioned dialysis apparatuses are the known single-needle dialyzers as disclosed for example in U.S. Pat. Nos. 3,811,800, 3,791,767 or DE-OS No. 2,455,917. With the aid of such apparatuses blood is intermittently pumped around a closed circuit and with the aid of the blood pump an excess pressure is produced in the closed circuit which effects the ultrafiltration of plasma water in the hemofilter.

Accordingly, in medicine arteriovenous hemofiltration was found to be a considerable simplification because it does not require any control unit. In this method, both an arterial and a venous access is made surgically and therebetween an extra corporeal circulation is established which includes a hemofilter. With a closed cycle the blood flow rate depends on the flow resistance of the extracorporeal system and the arteriovenous pressure difference whilst the filtration performance depends on the filtration properties of the filter and the venous pressure. The system is constructed so that the filtrate can flow into a collection bag or vessel and from time to time the amount collected measured and checked.

Although it is simple, this system has some serious disadvantages.

Firstly, the extracorporeal circulation is not monitored in any way. Since an arterial connection is present there is therefore an acute danger of loss of blood into the surroundings if a defect occurs in the system or a connection becomes detached.

This can lead to the patient bleeding to death within a few minutes if the extracorporeal cycle is not closed again in good time.

Furthermore, the filtration performance, apart from the choice of the hemofilter and hose material used, cannot be controlled and monitored. This basic disadvantage leads to the filtration performance being low when the hyperhydration is high and the blood pressure has dropped and increasing again only with increasing dehydration and increasing blood pressure. Accordingly, a hyperhydrated patient can only be brought slowly out of a shock due to hyperhydration but fall all the more rapidly into a state of shock induced by excessive dehydration. Thus, in this respect the filtration performance in conventional arteriovenous hemofiltration behaves exactly oppositely to the desired behaviour.

SUMMARY OF THE INVENTION

The problem underlying the invention is therefore to provide an apparatus of the type mentioned at the beginning in which with small technical expenditure a volume-controlled dehydration of blood is possible.

The invention is further based on the problem of constructing the aforementioned apparatus in such a manner that a balanced supply of substitution solutions is also possible and that in particular the ultrafiltration and the balancing can be automatically monitored and controlled.

This problem is solved according to the invention in that the filter comprises at its filtrate connection an ultrafiltrate measuring chamber.

Compared with arteriovenous hemofiltration the apparatus according to the invention firstly has the advantage that it is conveniently operated with a venous access so that as a rule there is no danger of bleeding to death. As usual in dialysis, such an access may be established in simple manner, which represents a further advance over arteriovenous hemofiltration because with the latter method complicated femoral catheters must be inserted.

Furthermore, the apparatus according to the invention imposes its mode of operation onto this filtration method so that the filtration performance and rate is determined solely by the apparatus according to the invention and practically not by the blood circulation of the patient to be treated, as is the case with arteriovenous hemofiltration. Consequently, a hyperhydrated patient can be dehydrated with the apparatus according to the invention considerably quicker than is the case with arteriovenous hemofiltration. This independence from the control of the blood pressure of the patient represents a substantial improvement in this type of hemofiltration, especially since particularly in critical situations arteriovenous hemofiltration has limited applications because the blood pressure is too weak.

The apparatus according to the invention cannot only perform hemofiltration; at the same time it can effect exact balancing so that equal parts of infusion solution and filtrate can be supplied to the body and withdrawn therefrom.

Considered overall, the entire apparatus is very simply constructed compared with complicated dialysis machines and is therefore suitable for any intensive care department. Thus, for example, the entire tubing system including the pump chamber and the hemofiltrate measuring chamber consists of a disposable system which can be supplied sterile and discarded after use. By expediently applied markings this disposable system can be associated in simple manner with the corresponding parts of the apparatus according to the invention even by relatively unskilled personnel and this is a decisive advantage as regards easy operation.

Finally, the apparatus according to the invention can be conveniently monitored with the aid of a microprocessor which immediately detects even small blood leaks or apparatus faults, such as a blockage in a line section or the filter, and then initiates a corresponding alarm or shuts off the apparatus.

Further details, advantages and embodiments will be explained in the following description of several examples of embodiment with the aid of the drawings, wherein:

DESCRIPTION OF SPECIFIC EMBODIMENTS

Figure 1:
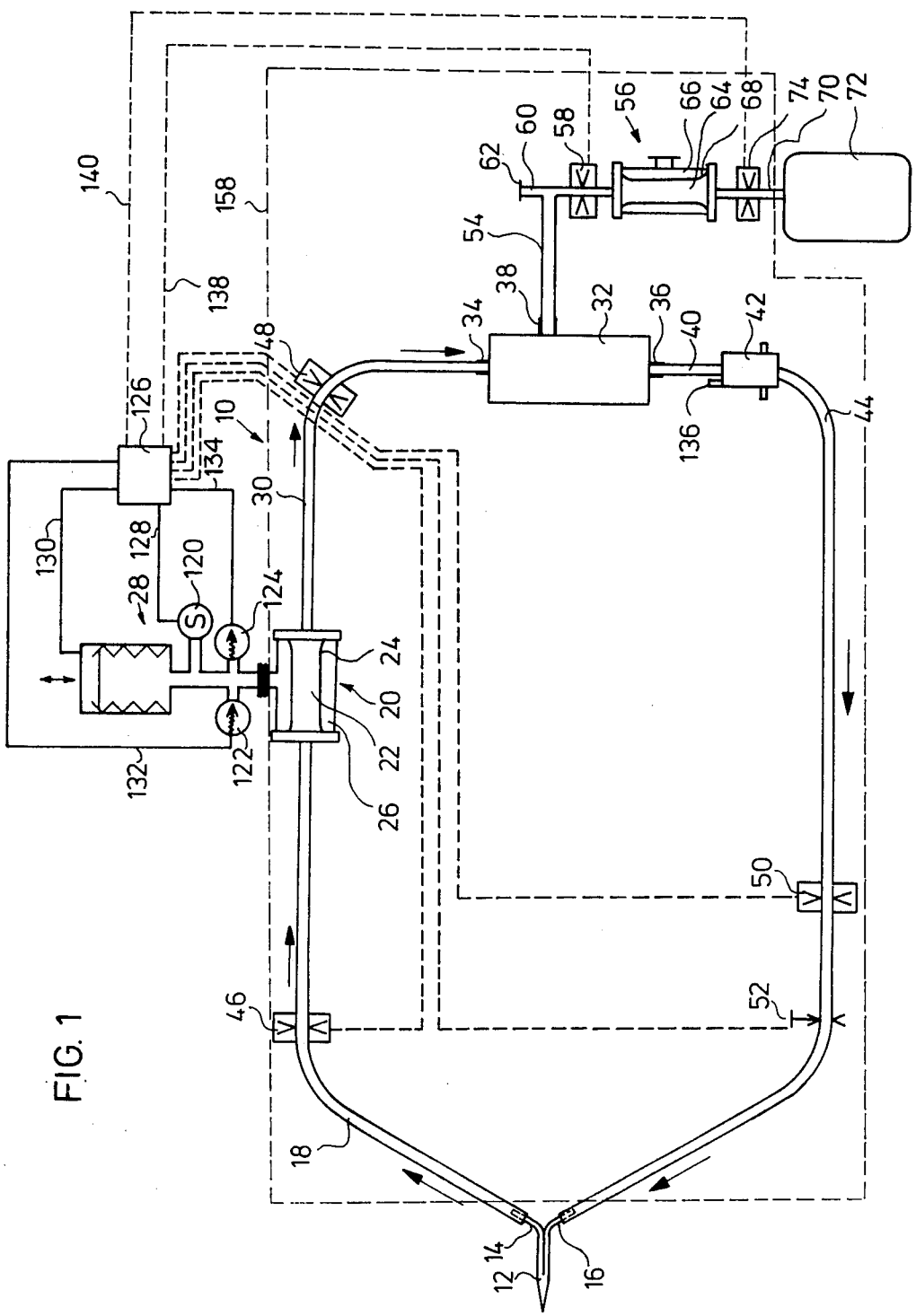
FIG. 1 shows diagrammatically a first embodiment of an apparatus for removal of water from blood.

In FIG. 1, 10 denotes an apparatus for removing water from blood in a first embodiment. This apparatus 10 comprises firstly a hollow cannula 12 with which a blood connection to a vein can be established. According to the embodiment shown in FIG. 1 this cannula 12 is made Y-shaped at its other end and thus forms two connections 14 and 16 which can be connected to corresponding tube lengths. Advantageously, it is constructed as a simple needle which branches accordingly, the mixing effect being practically negligible.

The connection 14 of this cannula 12 serves for the withdrawal of blood and is connected to a first flexible tube 18. The other end of said flexible tube 18 is connected to the pump chamber 20 which will be described in detail hereinafter. Said pump chamber 20 advantageously comprises two inner spaces divided from each other, i.e. the chamber portion 22 and the chamber portion 26 separated from said chamber portion 22 by a flexible wall 24. The chamber portion 22 is in flow connection with the flexible tube 18 whilst the chamber portion 26 is connected to a bellows pump 28.

The pump chamber 20 is connected downstream to a further flexible tube 30, said tube 30 in turn being in flow connection with the chamber portion 22 and the tube 18. The other end of said tube 30 opens into a filter 32 which is preferably constructed as a hemofilter and consequently has three connections, i.e. connection 34 connected to the tube 30, the outlet 36 and the filtrate outlet 38.

This filter is advantageously constructed as a hemofilter in which excess plasma water is pressed through the membranes provided in the filter and separated at the filtrate outlet 38. Advantageously, said filter 32 comprises a plurality of membrane-like hollow filaments through which the blood is conducted, the filtrate being pressed out at the membrane wall thereof.

The outlet 36 is connected to the flexible tube 40 whose other end is connected to an air separation chamber 42.

The air separation chamber 42, in which for safety reasons excess air is removed, is connected at its bottom outlet to the flexible tube 44 which is returned to the connection 16 of the cannula 12.

Thus, the flexible tube 18, the chamber portion 22 of the pump chamber 20, the flexible tube 30, the filter 32, the flexible tube 40, the air separator 42 and the flexible tube 44 represent a closed circuit in which the blood can circulate, i.e. is pumped from a blood connection in a cycle sealed from the atmosphere to a further blood connection. The invention can be used in a circuit having at least one blood connection with the patient.

Since according to this embodiment only a single blood connection is established by means of the cannula 12 the supplying and withdrawal of blood can usually take place only intermittently so that corresponding means are to be provided for blocking the supply and withdrawal of blood in the tubing system.

The flexible tube 18 can be opened and closed by a clamp 46 and the flexible tube 30 opened and closed by a clamp 48, said clamps 46 and 48 operating in opposition for example, under supervision of a monitoring device 126 functional as a controlling means and coupled to valves 46 and 48.

Furthermore, the flexible tube 44 can be opened and closed by the clamp 50 under supervision of monitoring device 126 coupled to valve 50. At the same time, downstream of the clamp 50 in the region of the flexible tube 44 a throttle means 52 is provided with which the amount of blood flow through the tubing system upstream of the throttle means can be controlled.

Advantageously, the clamp 50 is controlled analagously to the clamp 48, i.e. in opposition to the clamp 46.

In addition, the throttle means 52 can be adjusted, preferably manually, so that the desired excess pressure is generated in the tubing system upstream.

The throttle (52) can be controlled by control means (126) to establish a predetermined excess pressure in the extracorporeal circulation circuit between clamp (46) and the throttle (52).

The filtrate outlet 38 of the filter 32 is connected to a flexible tube 54 whose other end is connected to the filtrate measuring chamber 56.

Conveniently, the flexible tube 54 can be clamped and opened again by a clamp 58, the actuation of this clamp 58 in normal operation preferably corresponding to the phase of the clamps 48 and 50.

The flexible tube 54 further comprises a vent tube 60 which is sealed with a bacteria-blocking air-permeable membrane which conveniently consists of a microporous hydrophobic membrane of PTFE and the like, the pore diameter being less than 1 $\mu$m.

Preferably, the filtrate measuring chamber 56 is substantially similar to the pump chamber 20 and in particular comprises a chamber portion 64 and a chamber portion 66 which are separated from each other by a flexible wall 68.

The chamber portion 64 is in flow connection with the flexible tube 54 on the one side and on the other side with the flexible tube 70 whose other end is connected to a collection bag 72. There is thus a fluid connection between the tube 54, the chamber portion 64, the tube 70 and the connection vessel 72 in which the filtrate formed is finally collected.

Advantageously, the flexible tube 70 may also be shut off by a clamp 74 which operates in phase with the clamp 46 and in opposition to the clamps 48, 50 and 58.

Figure 2:
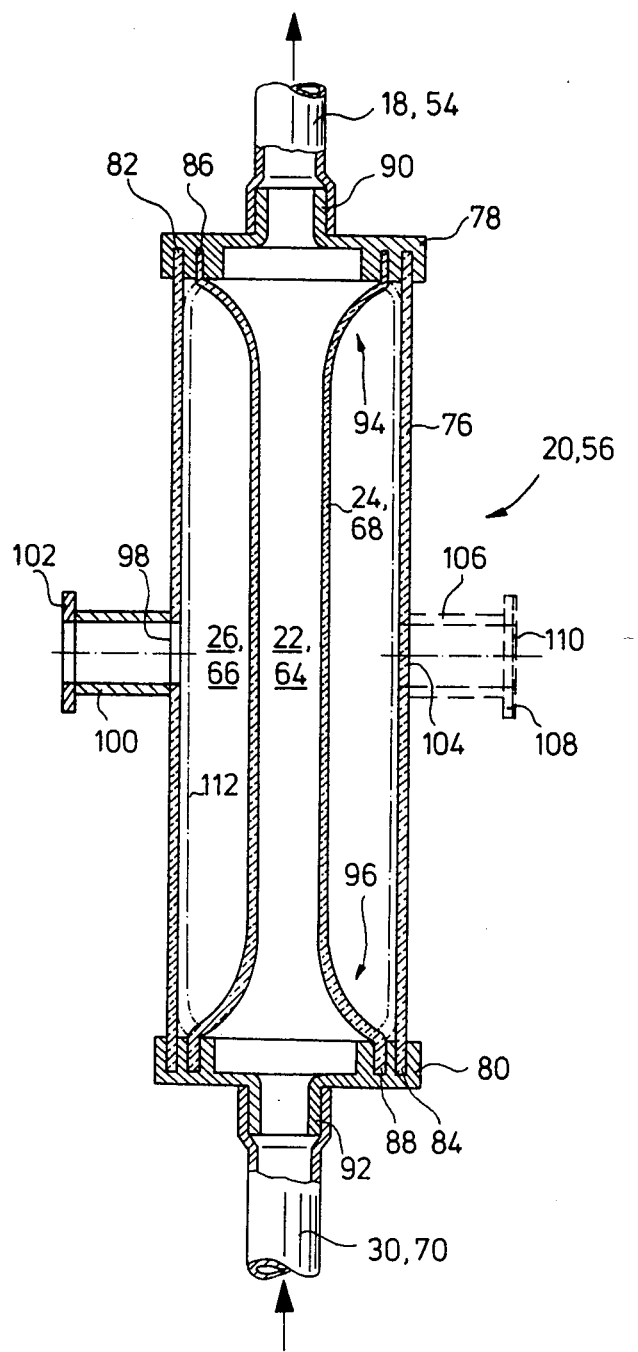
FIG. 2 is a longitudinal section through a blood pump or ultrafiltrate measuring chamber.

FIG. 2 shows the pump chamber 20 according to the invention in longitudinal section which in a preferred embodiment substantially corresponds in its basic configuration to the filtrate measuring chamber 56. As explained above, the chamber 20, 56 comprises separate portions 22, 64 and 26, 66 respectively which are separated by a flexible wall 24, 68.

The chamber 22, 56 consists substantially of a rigid preferably transparent tube 76 closed at both its ends by end plates 78 and 80. Provided in each of these end plates 78 and 80 are annular grooves 82 and 84 respectively into which the tube 76 is inserted in bonded and sealing manner so that it represents a sealed body.

The end plates 78 and 80 each comprise a further concentric inner annular groove 86 and 88 into which the tubular flexible wall 24, 68 is likewise inserted in bonded sealing manner so that there is no flow connection between the chamber portions 26, 66 and 22, 64.

The end plates 78 and 80 are also provided with a fluid passage in the form of a connection piece 90 and 92 which can be connected to the tubes 18, 30 and 54, 70 respectively so that the flow connection described above is obtained.

According to the embodiment illustrated in FIG. 2 the hose-like flexible wall 24, 68 is transversely tensioned in the end regions 94, 96 in the same manner as a rubber hose and secured in the annular groove 86 and 88. However, in the center region of the tube 76 it is at the most somewhat tensioned in the longitudinal direction but not in the transverse direction so that it does not form folds or the like.

This manner of attaching the hose-like flexible wall is preferred but not critical. Accordingly, other hose securing methods may also be employed. Thus, for example, the hose or flexible wall can be inserted into the tube 76 even without transverse tension and only with slight longitudinal tension or even free of tension.

As already mentioned, the tube 76 is preferably made rigid, i.e. it does not yield to the partial vacuums and excess pressures employed. In order to exert a reduced or excess pressure on the flexible advantageously hose-like wall 24 and to operate basically relieved of pressure in the annular sealed space of the chamber portion 26, 66, the tube 76 is traversed by at least one opening 98 which is followed on the outside by a connecting piece 100 having a flange 102.

If the chamber 26, 66 is to be provided with one outlet and one inlet, a further opening 104 and a further connecting piece 106 having a flange 108 are provided, as shown in dashed line in FIG. 2. The flange 108 can be covered with a bacteria-impermeable filter 110 and therefore permits pressure compensation of the chamber portion 26, 66. This filter 110 corresponds to the microporous membrane 62 which is mentioned above and which by the way advantageously does not allow water to pass until an excess pressure of about 1 bar is reached.

As indicated in FIG. 2 by 112 the hose-like wall 24, 68 on application of a partial vacuum via the connecting piece 100 can expand to such an extent that it can bear directly on the inner wall of the tube 76. On the other hand, it returns due to its returning force into the initial condition as shown in FIG. 2 again and under a corresponding excess pressure which again can be applied via the connecting piece 100, can also be completely pressed together. Thus, the interior of the tube 76 can practically be completely filled and again emptied.

For the hose used as separating wall 24, 68 highly elastic materials are used, in particular organic polymers and their mixtures, such as polyurethanes, caoutchoucs, silicone caoutchoucs, latex, rubber, regenerated rubber, and the like. Preferably, latex or a silicone rubber called Silastic is used which if necessary may include additives and agents improving the elasticitiy. Advantageously, the wall of this hose can be expanded to such an extent that the inner volume with respect to the non-expanded condition of the hose can be increased by at least five times, in particular ten times.

Accordingly, according to a preferred embodiment the hose can additionally accommodate up to ten times its inner volume.

The wall thickness of such a hose is substantially not critical and lies in a range of about 0.05-0.5, preferably 0.1-0.4 mm. The wall thickness and the hose material are selected in dependence upon the desired pressure characteristic and the volume expansion. Thus, the wall thickness of the hose is the greater the higher the initial pressure to be applied.

According to a preferred embodiment a hose is selected which decreases in its wall thickness from the one end to the other as shown for example in FIG. 2 itself. Consequently, the hose first inflates at the end having the smallest wall thickness. The pressure characteristic of such a hose is shown for example in dashed line in FIG. 3. Accordingly, at first a considerable vacuum must be applied in order to increase the volume of the hose by about 1-2 ml. This vacuum increases only slightly until the volume of the hose is at about 20-22 ml. This is where the complete filling of the hose is achieved so that when a greater vacuum is applied practically no further increase in the inner volume of the hose can be achieved. Accordingly, the hose, as illustrated in FIG. 2 at 112, bears on the inner wall of a tube 76.

A hose of the type mentioned above whose wall thickness decreases over the entire length of the chamber by up to 50% can for example be produced by dipping a rod into a liquid polymer composition for making such a hose, for example latex, and then withdrawing the rod from the liquid composition. Due to the liquid state of the composition part of the latter flows down the rod so that the wall thickness of the hose or flexible tube thus obtained increases continuously from one end of the hose to the other.

The hose volume and the length thereof depend on the use and design of the apparatus. Usually, the diameter of a hose lies in a range of 5-15, preferably about 8 mm, whilst the length of the hose can be 5-20 cm. However, shorter or longer dimensions are conceivable if required by the specific use. If only small blood volumes are conveyed the hose used will have correspondingly smaller dimensions than with larger blood throughputs.

As already explained above, however, the volume of the fluids circulated in the chambers 20, 56, i.e. blood and filtrate, depends on the inner volume of the tube 76 which is defined by the end plates 78, 80. The volume $V_1$ of the chamber 20 formed from the chamber portions 22 and 26 and the inner volume $V_2$ of chamber 56 formed from the chamber portions 64, 66 determine by their ratio the proportion of the ultrafiltrate in the entire blood amount circulated. With hyperhydrated patients this ratio may be 3:1, i.e. with a blood pump chamber 20 of 30 ml content the ultrafiltration measuring chamber 56 can have a content of 10 ml. Preferably, the ratio of $V_1:V_2$ is kept within a range of 5:1 to 2:1.

Correspondingly, the volume $V_1$ or $V_2$ may be up to 80 or 40 ml respectively whilst the elastic hose in the pressureless state contains about 5-15 ml.

It should be mentioned that as material for the resilient hose all water-impermeable materials having a correspondingly high breaking elongation (>200%) are suitable, the aforementioned materials belonging in this class.

Materials suitable for the tube 76 are those which when suitably dimensioned are resistant to pressure and substantially rigid. This includes for example polymeric materials such as polyethylene, acrylic glass, PVC and the like.

According to the embodiment illustrated in FIG. 1 the pump chamber 20 is connected to a bellows pump 28. The connection and the bellows pump 28 itself are shown in more detail in FIG. 4. The flange 102 of the connecting piece 100 is connected to a correspondingly matching flange 114 of the bellows pump 28.

A bellows pump 28 means a pump with constant displacement or working volume. Preferably, a bellows pump is used whose working volume is greater than the inner volume of the tube 76 of the pump chamber 20. Particularly preferred is a bellows pump whose working volume is more than 20% greater than that of the storage volume of the pump chamber 20.

By means of the bellows pump 28 the air is withdrawn from the chamber portion 26 through the opening 98, the connecting piece 100 and the tube 116 adjoining the flange 114 into the bellows 118.

This pump 28 can be controlled by pressure or also in constrained manner.

In the pressure-controlled embodiment a switching of the pump, which of course need not necessarily be constructed as bellows pump, occurs at a predetermined upper and lower pressure value within the chamber portion 26. The pump can either be switched off when the portion 22 is full of blood, air entering the chamber portion 26 via a corresponding vent valve, not shown, and the resilient hose-like wall 24 returning to its initial state, pumping off blood, or switched into the pumping-off position, wherein by the supplying of air by means of the pump 28 the elastic wall 26 can again be detensioned.

For determining a predetermined partial vacuum in the pump system, in particular in the chamber portion 26 or the connecting piece 100 and tube 116 in connection therewith, a pressure sensor 120 is provided with which the pump can be switched at a predetermined reduced or excess pressure.

In a forced or constrained control, in which the bellows pump oscillates between upper and lower dead center, i.e. a maximum and minimum pressure value, such a pressure sensor 120 is not necessarily required but is advantageously employed for monitoring the system. Expediently, however, the reduced pressure and excess pressure in the chamber portion 26 or the entire pump chamber 20 is controlled with a vacuum valve 122 and an excess pressure valve 124. These pressure valves 122 and 124 open automatically when a predetermined pressure is reached. Thus, the vacuum valve 122 will preferably be set so that it switches when the hose-like elastic wall 24 has completely filled with blood and come to bear at 112 on the tube 76.

Due to the preferred overdimensioning explained of the bellows pump 28 with respect to the pump chamber 20 it first moves further up to the top dead center and does not switch over until the latter is reached. When the switching takes place at the top dead center the blood is carried away out of the pump chamber 20, this being done in such a manner that the chamber portion 22 is emptied before the bottom dead center is reached. For controlling the resulting excess pressure the aforementioned excess pressure valve 124 is provided which opens when the chamber portion 22 has been emptied.

A system having a similar pump chamber and a similar bellows pump in a single-needle system is described for example in German patent application P No. 32 05 449 and express reference is made to the disclosure of said application.

The mode of operation of the apparatus 10 according to FIG. 1 will be described below.

In the normal course of the filtrate program the clamps 46 and 74 are opened whilst the clamps 48, 50 and 58 remain closed. The bellows pump 28 is at its bottom dead center and is started to initiate the suction operation. The bottom dead center, which arises automatically in operation with constrained control, also refers to the switching point of the pump at which in pressure-controlled operation the switching to another mode of operation takes place.

The bellows pump 28 now sucks blood via the hollow needle 12 and the tube 18 into the chamber portion 22 because the partial vacuum produced in the chamber portion 26 by the expansion of the bellows 118 expands the hose-like flexible wall 24. When this hose-like flexible wall has come to bear on the inner surface of the tube 76 either the vacuum valve 112 is opened or alternatively the pressure sensor 120 correspondingly switches the bellows pump 28. When the top dead center is reached and the bellows pump 28 switched over, the clamps 46 and 74 are closed and the clamps 48, 50 and 58 are opened.

By the compression of the bellows 118 an excess pressure is exerted on the chamber portion 22 filled with blood; said pressure would rapidly return this blood through the return cycle to the hollow needle 12 if a flow resistance in the form of a throttle means 52 were not provided. This throttle means 52 thus produces in the circuit following the pump chamber a predetermined excess pressure which effects a predetermined ultrafiltration in the filter 32. By corresponding control of the excess pressure or the compression duration with which the bellows pump 28 is operated the filtrate measuring chamber 56 is filled with expansion of the flexible wall 68. The air present in the chamber portion 66 is substantially removed in a pressureless manner through the filter 110 so that no counter pressure can build up in said chamber portion.

In the constrained control condition the chamber portion 22 is emptied from blood before the bottom dead center is reached so that the excess pressure can then abruptly increase, resulting in opening of the excess pressure valve 124. In the pressure-controlled condition this effects a switching at the sensor 120. Thereupon, the blood pump 28 is again switched to suction operation, as explained above, the clamps 46, 48, 50, 58 and 74 being reversed accordingly.

With the opening of the clamp 74 the ultrafiltrate measuring chamber 56 is emptied due to the return force of the elastic hose and the lower-lying vessel 72 and the ultrafiltrate therefrom flows into said bag 72 and is collected thereby.

The ultrafiltration rate is controlled by the blood flow, i.e. by the blood pumping rate. This depends of course on the yield of the shunt and can of course only be increased to the extent permitted by the blood access, for example a Shaldon catheter.

To ensure the ultrafiltration ratio given by the volume ratio pump chamber 20:ultrafiltration chamber 56, it must be monitored whether the pump chamber 20 is in fact filled and then discharged on each stroke of the bellows pump 28. For it is possible that due to inadequate yield of the blood connection the pump chamber is not filled in the given time interval. It is further conceivable that either the flexible tube 18 buckles or one of the tubes 30, 40 or 44 is buckled or the filter 32 is blocked, for example because the blood coagulates.

For this purpose, the pressure sensor is coupled to a monitoring device 126 via the line 128 and said device receives at each dead center control signals from the bellows pump 28 via the line 130.

The following explanation assumes that the bellows pump 28 is positively controlled in constrained manner as is the case in the preferred embodiment. It is assumed that at the start of the monitoring operation the bellows pump 28 is compressed to the value $p_1$ and the pressure which has built up therein is set by the excess pressure valve 124. This pressure $p_1$ is stored in a microprocessor provided in the monitoring device 126.

By the expansion of the bellows pump 28 the pressure in the pump chamber continuously decreases, blood being sucked off. When the instant $t_1$ is reached the pump chamber is fully expanded so that the vacuum valve 122 opens at the partial vacuum $p_1$.

Notification of the actuation of the excess pressure and vacuum valves 122 and 124 is also passed to the monitoring device 126 via the lines 132 and 134.

Since at the point of opening of the vacuum valve 122 the bellows 118 has not yet reached its dead center the pressure $p_2$ is kept constant until this point is reached. On reaching the top dead center a corresponding control signal is again emitted to the monitoring device 126 which then measures the time $t_2$ within which the bellows 118 is compressed until the excess pressure valve 124 opens and furnishes a corresponding signal to the monitoring device 126. In addition, the total cycle time $t_3$ is measured.

It is possible to see whether the system is blocked from the pressure variation and the ratio $t_1:t_3$, i.e. the ratio of the effective suction time to the cycle time of the system.

For if the tube 18 is buckled no blood can be extracted and firstly the pump chamber 20 cannot expand. As a result, the partial pressure at the pressure monitor 120 drops much more quickly and the vacuum valve 120 opens before the time $t_1$ is reached.

Similar conditions obtain during compression of the bellows 118. In this case as well, in the proper operating state a certain ratio of compression time $t_2$ to cycle time $t_3$ will arise which is greatly reduced when the pump line is interrupted or the filter 32 blocked.

Figure 4:
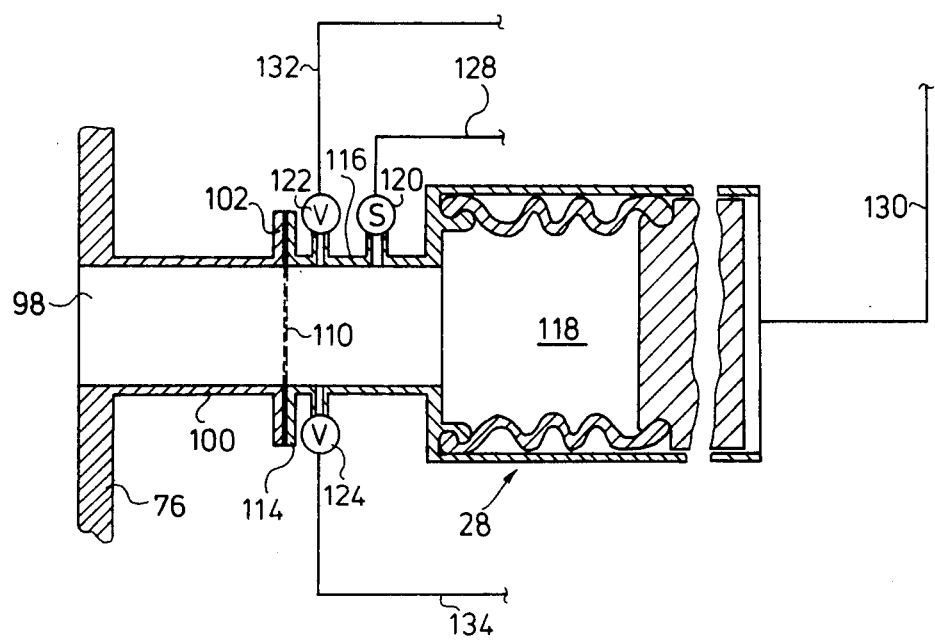
FIG. 4 is a longitudinal section through a diaphragm pump for use in the arrangement shown in FIG. 1

As a result, the monitoring device 126 can also detect the occurrence of small leaks in the system which lead to blood being lost to the surroundings. This loss to the surroundings is made more difficult for example from the pump chamber 20 because as shown in FIG. 4 a hydrophobic filter 110 is provided between the flanges 102 and 114, said filter being permeable to air but impermeable to blood and water.

Advantageously, it is also possible with the monitoring device 126 to carry out a program which controls the starting-up phase. During this phase, for example within 5 minutes, the apparatus must be synchronized by the user and possibly adjusted. Thus, for example, the rate of the pump 28 or the degree of throttling with the throttling means 52 can be regulated. At the end of the starting-up phase the user certifies that everything is in proper order. From this point on, the microprocessor records the pressure cycle designated as correct. If the pressure differs too much from the initial value an alarm is initiated and all functions stop, all the clamps being closed.

As already explained above an air separator 42 is provided in the extracorporeal system to prevent the danger of an air embolism. Such an air separator chamber is for example known from DE-OS No. 3,115,299 and express reference is made to the disclosure and mode of operation thereof. Since an excess pressure usually obtains in the air separator 42, if no alarm case is present, no emptying of the chamber occurs if the air separated from the blood in the chamber is removed through the hydrophobic filter 136. At the excess pressures obtaining said hydrophobic filter prevents a passage of blood or plasma because a hydrophobic microporous membrane of PTFE with pore sizes beneath 1 $\mu$m and a water entry pressure of more than 1 bar is used.

Advantageously, the entire system except for the bellows pump 28 separable from said system is prepared sterile as disposable system in one piece, the individual tubing sections being marked in colors to facilitate insertion in correspondingly color marked parts of the apparatus. The operator's task is then only to insert the tubes 18, 30, 44, 54, 70 into the clamps 46, 48, 50, the throttling means 52, the clamp 58 and the clamp 74, insert the tubes 30 and 40 in the hemofilter 32 and insert the tubes 40 and 44 in the air separator 42 and connect the bellows pump 28 to the pump chamber. Before starting treatment the system must be filled with physiological saline solution. It therefore advantageously includes a filling program.

During the filling program the clamps 58 and 74 remain closed whilst the clamps 46, 48, 50 and the throttling means 52 are opened.

A bag containing saline solution is attached to the Y-shaped hollow cannula 12 and the bellows pump begins to pump. It now sucks in an air-fluid mixture for a time, the mixture always being returned to the saline container. Part of this mixture is filtered in the filter 32 and therefore fills the tube 54 up to the clamp 58, the air present in the tube and in the filter 32 advantageously being removed via the membrane 62. However, this membrane 62 may also be omitted if a small error in the ultrafiltration rate determination can be accepted.

The air contained in the system is separated from the fluid in the air separator 42 and removed therefrom as mentioned above. This specifically controlled filling operation prevents the collection bag 72 from being pumped full with air.

At the end of the treatment the blood present in the system must be returned to the patient. For this purpose, as is otherwise also usual, the tube 18 is separated from the cannula 12, the connection 14 being closed. Said tube 18 is again attached to the saline bag and the pump operation again started, the throttling means 52 being completely opened to largely prevent an ultrafiltration. At the same time the clamps 58 and 70 are closed again. Accordingly, the starting and emptying program are practically identical.

In a further embodiment of the apparatus 10 as shown in FIG. 1 the air separator 42 may also be omitted if it is ensured that no artificially produced partial vacuum occurs at all in the entire extracorporeal circulation. For this purpose, the vacuum valve 122 must be adjusted so that it reliably opens already at +10 mm Hg. Furthermore, of course, the elastic wall 24 must be so adjusted that it is fully pumped up even by the relatively low venous blood pressure of the patient. To check this, either an optical check at the start of the treatment is necessary or an automatic check of the filling of the elastic expansion vessel must be carried out as mentioned in German patent applications P Nos. 32 05 449 and 31 31 075, to the disclosure of which express reference is made.

It should also be mentioned that the monitoring device 126 can also automatically store the number of cycles with which the pump 28 is operated. By a suitable preselection the ultrafiltrated amount can be defined and thus a defined dehydration of the patient carried out.

Such a preselection is moreover also possible with arteriovenous ultrafiltration. In this embodiment the tube 30 is connected to the artery and the tube 40 directly to the vein whilst the filtrate cycle as shown in FIG. 1 remains the same. Only the clamps 58 and 74 are connected to the monitoring device 126 via the lines 138 and 140 and this device stores the cycle number accordingly and closes down the clamps when the predetermined number of cycles has been reached. Such a control of the monitoring device 126 need not necessarily be provided.

In a further embodiment of this arteriovenous hemofiltration the clamps 58 and 74 are mechanically driven by a cam, and it is again possible to record accordingly the closure and opening cycles. Thus, by a suitable choice of the cycles the desired ultra-filtrate amount to be filtered off can be predetermined.

Figure 5:
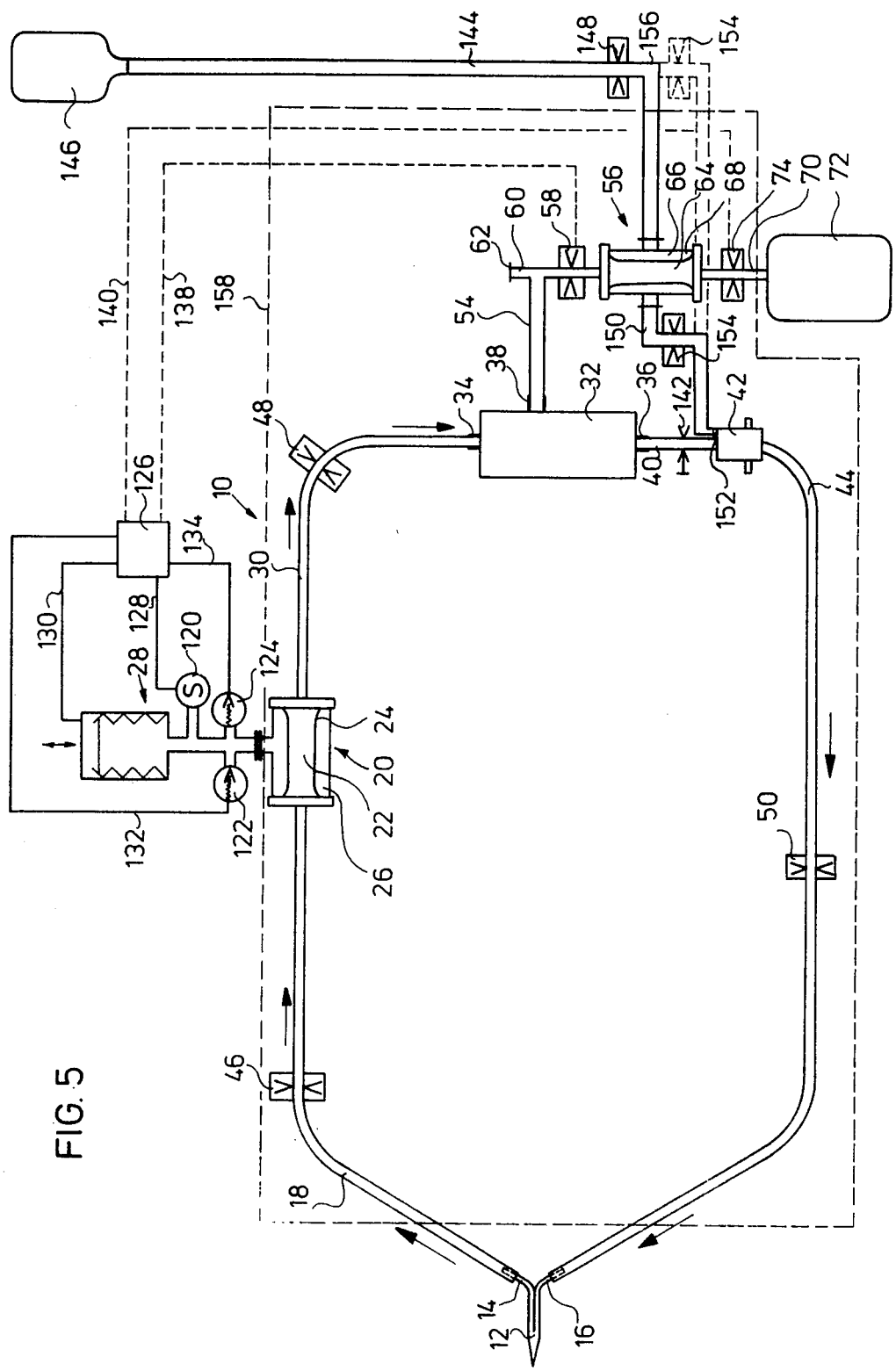
FIG. 5 is a further schematic illustration of another embodiment of the apparatus for removing water from blood.

FIG. 5 shows a further embodiment of the apparatus according to the invention which is based substantially on the embodiment according to FIG. 1. However, in contrast to the embodiment shown in FIG. 1 it permits balancing of filtrate and substitution solution to be supplied.

As explained at the beginning pronounced hyperhydration of patients is due to the administration of high-caloric parenteral substitution solutions. The apparatus according to FIG. 1 dehydrates patients who are already hyperhydrated without however being able to balance exactly the administration of substitution solutions.

The embodiment according to FIG. 5 remedies this and balances exactly the administration of substitution solutions.

Figure 3:
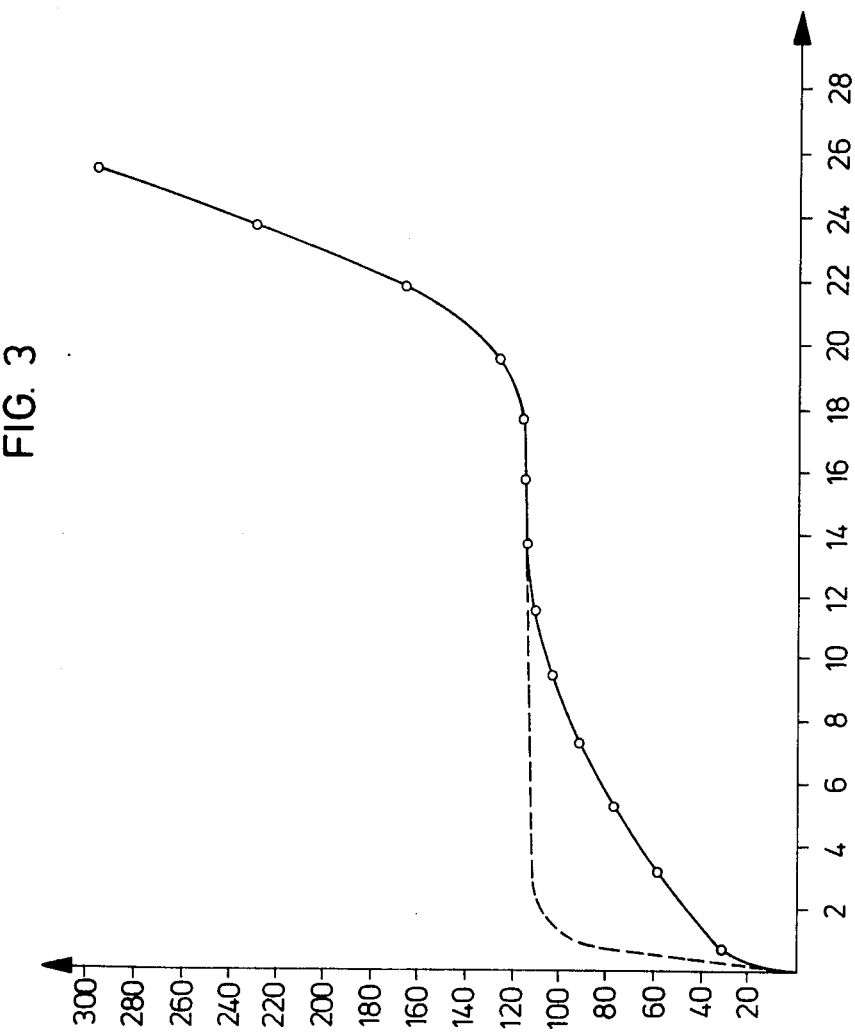
FIG. 3 shows a pressure/volume characteristic of a measuring chamber as shown in FIG. 2.

In the embodiment illustrated in FIG. 5 the modification compared with the embodiment of FIG. 1 is shown only diagramatically. The throttle 52 provided downstream of the air separator 42 according to FIG. 1 is replaced by a throttle 142 which upstream of the air separator partially blocks the tube 40. The ultrafiltrate measuring chamber shown according to FIG. 3 is connected via the connecting piece 100 and a tube 144 to the infusion bag 146. This tube 144 can be shut off and opened by a clamp 148.

Furthermore, the second connecting piece 106 is connected via a tube 150 to the infusion connecting piece 152, through which heparin can also be introduced, to the air separator 42. This tube 152 can be closed by the clamp 154.

If the ultrafiltrate measuring chamber 56 has only one connecting piece, for example 100, the tube 144 branches at 156 and the tube 150 is attached at this point. This is indicated in dashed line in FIG. 5.

The example of embodiment illustrated in FIG. 5 operates as follows:

In normal operation no air is present in the ultrafiltrate measuring chamber 56, i.e. ultrafiltrate is in the chamber portion 64 and infusion solution in the chamber portion 66. If the bellows pump at the lower dead center is now moved from the compressed state to the expanded state the clamps 46, 74 and 148 are again opened whilst the clamps 48, 50, 58 and 154 are closed. By this operation the chamber 64 filled with ultrafiltrate is emptied and at the same time infusion solution flows from the infusion bag or container 146 via the tube 144 into the chamber portion 66 and fills the latter.

When the pump has reached the top dead center the clamps 46, 74 and 148 are closed and the clamps 48, 50, 58 and 154 are opened.

The ultrafiltrate flowing into the chamber portion 64 expels the infusion solution disposed in the chamber portion 66 via the tube 150 into the air separator 42, i.e. an amount of infusion solution equivalent to the amount of ultrafiltrate is again added to the blood so that it is not possible at any time for hyperhydration of the patient to occur. This is a considerable technical advance in particular in the administration of high-caloric solutions.

The filling program for the infusion solution range is not critical because the air in the tubing can be removed via the air separator. Usually, the clamps 148 and 154 are advantageously closed in the starting and emptying program.

Furthermore, this system is also available sterile as disposable tubing system in one piece so that it is only necessary to connect the tube 144 to the infusion solution container 146.

To make the entire tubing system particularly simple to handle said system, possibly including the filter 32, the filtrate measuring chamber (56), and the air separator (42) is combined in a cassette shown in dashed line at 158 in FIGS. 1 and 5 and advantageously consisting of plastic material and out of which only the three tube connections 18, 44 and 70 according to FIG. 1 and four tube connections 18, 44, 70, 144 according to FIG. 5 project. Said cassette 158 can be easily inserted into apparatus 10 and is then ready for operation in the inserted condition. Advantageously, the apparatus 10 and cassette 158 are so designed that all the connections functionally established to the bellows pump 28 or to the shut-off clamps 46, 48, 50, 58, 74 148, 154 and to the throttle means 52 or 142 are established by the insertion operation. This is achieved by corresponding recesses, not shown, at the bottom of the cassette 158.

I claim:

1. In an apparatus for removing water from blood including an extracorporeal circulation circuit, said extracorporeal circulation circuit having a blood inlet side and a blood outlet side, a supply line on the blood inlet side and having an upstream end and a downstream end, an offtake line on the blood outlet side and having an upstream end and a downstream end, and a filter having a filtrate side and a blood side, said filter being connected to said downstream end of said supply line and said upstream end of said offtake line, said upstream end of said supply line and said downstream end of said offtake line being connected to at least one blood connection, said supply line including therein a blood pump, a first clamp disposed upstream of said blood pump and a second clamp disposed downstream of said blood pump, said offtake line further including therein a third clamp, the improvement comprising:

a filtrate connection (38) on said filtrate side connected to said filter (32);

an inlet tube (54) connected to said filtrate connection (38);

means for limiting the volume of water removed from blood in the circuit in one machine cycle to a predetermined volume $V_2$, said limiting means comprising an ultrafiltrate measuring chamber (56), said ultrafiltrate measuring chamber having an inlet connection coupled to said inlet tube (54) and an outlet connection, said ultrafiltrate measuring chamber (56) being coupled at its inlet connection through said inlet tube (54) to said filtrate connection and having a restricted maximum intake volume $V_2$;

an inlet tube (70) coupled to said outlet connection;

a fourth clamp (58) on said inlet tube (54) and a fifth clamp (74) on said outlet tube (70); and control means (126) coupled to said first clamp, to said second clamp, to said third clamp, to said fourth clamp and to said fifth clamp, said control means (126) being operative to open and close said first clamp and said second clamp in opposition to one another, to open and close said third clamp in synchronism with said second clamp, to open and close said fourth clamp in synchronism with said second clamp, and to open and close said fifth clamp in synchronism with said third clamp, said control means being presettable to actuate said clamps (46, 48, 50, 58, 74) during a treatment to specify total amounts of fluid to be withdrawn from a patient through said ultrafiltrate measuring chamber;

and wherein said blood pump includes a pump chamber (20) in said extracorporeal circulation circuit, the maximum intake volume $V_1$ of the pump chamber (20) and the maximum intake volume $V_2$ of the ultrafiltrate measuring chamber (56) are in a ratio of between 5:1 and 2:1, thereby controlling the ratio of the amount of blood pumped in a machine cycle to the amount of water removed in a machine cycle.

2. Apparatus according to claim 1 wherein said inlet tube (54) further comprises a vent tube (60) sealed with a hydrophobic microporous bacteria blocking membrane (62).

3. Apparatus according to claim 1 further comprising an air separator (42) disposed downstream of the filter (32), said air separator (42) being vented via a hydrophobic microporous bacteria-blocking membrane (136).

4. Apparatus according to claim 1, further including a throttle means downstream of said third clamp (50), and wherein said control means (126) is constructed and arranged to set said throttle means (52) to establish a predetermined excess pressure in the extracorporeal circulation circuit between the first clamp (46) and the throttling means (52).

5. The apparatus according to claim 1 wherein said ratio of the maximum intake volume $V_1$ and the maximum intake volume $V_2$ is 3:1.

6. Apparatus according to claim 1, further comprising a collecting bag (72) coupled to said outlet tube (70) from said ultrafiltrate measuring chamber.

7. Apparatus according to claim 6, including a subsystem comprising a cassette (158) detachably connectable to said at least one blood connection and to at least said collecting bag wherein said cassette has positioned and arranged therein at least the filter (32) and the filtrate measuring chamber (56), and wherein ends of said supply line, said offtake line and said outlet tube are positioned and arranged to provide fluid coupling from the cassette (158).

8. Apparatus according to claim 6, wherein said ultrafiltrate measuring chamber (56) is divided by an elastic wall (68) into a first chamber portion (64) in flow connection with said filter (32) and said collecting bag (72) and a second chamber portion (66).

9. Apparatus according to claim 8, wherein the elastic wall (68) is made in hose-form and its inner volume can be increased at least by a factor of 5 by expansion of the wall.

10. Apparatus according to claim 6, further including an air separator chamber (42) in said offtake line (40), a throttling means (142) in said offtake line (40) between said filter (32) and said air separator (42) and an infusion bag (146) in fluid communication with said air separator (42) and wherein said control means (126) is coupled to said throttling means (52) to constrict said offtake line (40) in a controlled manner.

11. Apparatus according to claim 10, wherein said infusion bag is coupled to an outer chamber portion (66) of said ultrafiltrate measuring chamber (56) via a first flexible tube (144) and wherein said outer chamber portion (66) is also coupled to said air separator (42) via a second flexible tube (150), said apparatus further including a sixth clamp (148) connected to selectively block and unblock said first flexible tube (144) and a seventh clamp (154) connected to selectively block and unblock said second flexible tube (150) and wherein said control means 126 is constructed and arranged to open and close said sixth clamp (148) synchronously with said first and fifth clamps (46 and 74) and said control means (126) is constructed and arranged to open and close said seventh clamp in opposite phase to said sixth clamp 150.

12. Apparatus according to claim 11, including a subsystem comprising a cassette (158) detachably connectable to said at least one blood connection and to at least said collecting bag, wherein said cassette has positioned and arranged therein at least the filter (32), the filtrate measuring chamber (56) and the air separator (42) and wherein ends of said supply line, said offtake line and said outlet tube are positioned and arranged to provide fluid coupling from the cassette (158), and wherein the cassette (158) further has positioned and arranged therein means for coupling said air separator (42) with said infusion bag, said coupling means projecting from the cassette (158).

13. Apparatus according to claim 1, wherein said pump chamber (20) has a means defining an inner pump chamber portion (22) formed therein, said means defining a pump chamber portion being positioned and arranged in said supply line of said extracorporeal circulation circuit so that blood can be supplied into the pump chamber portion (22) and expelled therefrom in discrete amounts controlled by maximum maximum intake volume $V_1$ of said pump chamber (20). and wherein said control means (126) specifies total amount of fluid withdrawn from a patient by actuating said clamps a specified number of times.

14. Apparatus according to claim 13, wherein said blood pump includes an air-driven bellows pump (28), operatively connected to said pump chamber (20) to supply an actuating fluid thereto, said bellows pump having a working volume which is greater than the maximum intake volume of the pump chamber (20).

15. Apparatus according to claim 14, wherein the working volume of said bellows pump (28) is more than 20% greater than the maximum intake volume of said pump chamber 20.

16. Apparatus according to claim 13, wherein said bellows pump (20) is pressure controlled.

17. Apparatus according to claim 16, further including a pressure sensor (120) positioned and arranged to measure pressure of said bellows pump and wherein said bellows pump (28) can be switched and monitored under the control of said pressure sensor (120).

18. Apparatus according to claim 16, further including a vacuum valve (122) and an excess pressure valve (124) positioned and arranged to regulate pressure in said bellows pump and wherein said bellows pump (28) can be set to a predetermined partial vacuum or excess pressure by said vacuum valve (122) and said excess pressure valve (124).

19. Apparatus according to claim 18, wherein said bellows pump (28), said pressure sensor (120), said vacuum valve (122) and said excess pressure valve (124) are connected to said control means (126) for automatic control of said extracorporeal circulation circuit.

20. In an apparatus for removing water from blood including an arteriovenous extracorporeal circulation circuit, said extracorporeal circulation circuit having a blood inlet side and a blood outlet side, a supply line on the blood inlet side and having an upstream end and a downstream end, and offtake line on the blood outlet side and having an upstream end and a downstream end, and a filter which is connected to said downstream end of said supply line and said upstream end of said offtake line, said upstream end of said supply line and said downstream end of said offtake line being connected to at least one blood connection, said supply line including a therein a blood pump, a first valve means disposed upstream of said blood pump and a second valve means disposed downstream of said blood pump, said offtake line further including therein a third valve means, said filter (32) having a filtrate side and a filtrate connection (38), the improvement comprising: means for limiting the volume of water removed from blood in the circuit in one machine cycle to a predetermined volume $V_2$, said limiting means including an ultrafiltrate measuring chamber (56), said ultrafiltrate measuring chamber (56) having an outlet conduit (70) and an inlet conduit (54) and being coupled through said inlet conduit (54) to said filtrate connection, said ultrafiltrate measuring chamber (56) having a restricted maximum intake volume $V_2$; a fourth valve means (58) in said inlet conduit (54) and a fifth valve means (74) in said outlet conduit (70); control means (126) coupled to said first valve means, to said second valve means, to said third valve means, to said fourth valve means and to said fifth valve means, said control means (126) being operative to open and close said first valve means and said second valve means in opposition to one another, to open and close said third valve means in synchronism with said second valve means, to open and close said fourth valve means in synchronism with said second valve means, and to open and close said fifth valve means in synchronism with said third valve means, said control means being presettable to actuate said valve means (46, 48, 50, 58, 74) during a treatment to specify total amounts of fluid to be withdrawn from a patient through said ultrafiltrate measuring chamber; an air separator chamber (42) in said offtake line (40); a throttling means (142) in said offtake line (40) between said filter 32 and said air separator (42); an infusion bag (146) in fluid communication with said air separator (42); wherein said control means (126) is coupled to said throttling means (52) to constrict said offtake line (40) in a controlled manner, and wherein said blood pump includes a pump chamber (20) in said supply line of said extracorporeal circulation circuit and the maximum intake volume $V_1$ of the pump chamber (20) and the maximum intake volume $V_2$ of the ultrafiltrate measuring chamber (56) are in a ratio of between 5:1 and 2:1, thereby controlling the ratio of the amount of blood pumped in a machine cycle to the amount of water removed in a machine cycle.

21. Apparatus according to claim 20, wherein said infusion bag is coupled to an outer chamber portion (66) of said ultrafiltrate measuring chamber (56) via a first flexible tube (144) and wherein said outer chamber portion (66) is also coupled to said air separator (42) via a second flexible tube (150) said apparatus further including a sixth valve means (148) connected to selectively block and unblock said first flexible tube (144) and a seventh valve means (154) connected to selectively block and unblock said second flexible tube (150) and wherein said control means 126 is constructed and arranged to open and close said sixth valve means (148) synchronously with said first and fifth valve means (46 and 74) and said control means (126) is constructed and arranged to open and close said seventh valve means in opposite phase to said sixth valve means (150).

22. The apparatus according to claim 20 wherein said ratio of the maximum intake volume $V_1$ and the maximum intake volume $V_2$ is 3:1.

* * * * *